(12) United States Patent
Ono et al.

(10) Patent No.: US 8,410,298 B1
(45) Date of Patent: Apr. 2, 2013

(54) PHOSPHORIC ACID ESTER PRODUCTION METHOD

(75) Inventors: Yuki Ono, Aichi (JP); Satoru Ono, Aichi (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 13/639,977

(22) PCT Filed: May 12, 2011

(86) PCT No.: PCT/JP2011/002658
§ 371 (c)(1),
(2), (4) Date: Nov. 27, 2012

(87) PCT Pub. No.: WO2011/142136
PCT Pub. Date: Nov. 17, 2011

(30) Foreign Application Priority Data

May 14, 2010 (JP) .................................. 2010-112649

(51) Int. Cl.
*C07F 9/02* (2006.01)
(52) U.S. Cl. ......................................................... 558/83
(58) Field of Classification Search ....................... 558/83
See application file for complete search history.

(56) References Cited

U.S. PATENT DOCUMENTS

2009/0227713 A1   9/2009   Kyoda et al.

FOREIGN PATENT DOCUMENTS

| JP | 2002-193986 | 7/2002 |
| WO | 2007/032277 A1 | 3/2007 |

OTHER PUBLICATIONS

International Search Report for corresponding International Application No. PCT/JP2011/002658 mailed Aug. 9, 2011.

*Primary Examiner* — Kristin Bianchi
(74) *Attorney, Agent, or Firm* — Renner, Otto, Boisselle & Sklar, LLP

(57) ABSTRACT

The present invention provides a novel production method which enables obtain a phosphorus compound having both an aromatic substituent and a phosphorinane backbone, without using an expensive hydrogen halide scavenger, without going through a complicated post treatment step or a step of recovering a solvent, and with a favorable yield and purity. In the present invention, step (1) of allowing phosphorus oxytrihalide to react with a phenol compound or naphthol compound at a molar ratio of 1.1-3.0:1 in the presence of metal halide, and removing unreacted phosphorus oxytrihalide, to produce a mono-substituted phosphorodihalidate; and step (2) of allowing the mono-substituted phosphorodihalidate obtained in the step (1) to react with a diol compound, at a 0.90 to 0.99 molar equivalent based on 1 mole of the halogen atom in the mono-substituted phosphorodihalidate so as to perform a dehydrohalogenation reaction, to obtain a phosphorus compound represented by Formula (V).

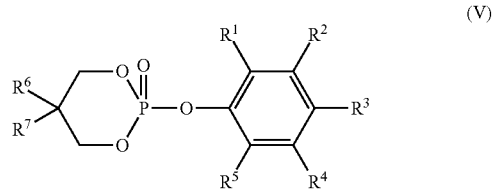

(V)

13 Claims, No Drawings

PHOSPHORIC ACID ESTER PRODUCTION METHOD

TECHNICAL FIELD

The present invention relates to a novel production method which enables to obtain a phosphoric acid ester, with a more favorable yield and purity compared to conventional methods, by allowing a phosphorus compound having both an aromatic substituent and a phosphorinane backbone to react in the presence of only metal halide, without using an expensive hydrogen halide scavenger, such as triethylamine, tributylamine or pyridine.

BACKGROUND ART

Phosphorus compounds have been broadly used for agricultural chemicals, plasticizing agents, flame retardants, metal extraction agents and the like, where the best of the specific characteristics thereof are brought out. Phosphorus compounds particularly have excellent functions as flame retardants, and are used in various synthetic resins, such as polyester, polycarbonate, ABS resins and polyurethane, and synthetic fibers, and the like. Phosphorus compounds cover a wide range of application.

Polyester fibers have excellent mechanical characteristics and easy processability, and thus, they have been used in various fields including clothes, interior, nonwoven fabrics, industrial materials and the like. In recent trends for increased awareness of disaster prevention, flame retardancy takes an important role in the use thereof for curtains, seats used in vehicles and the like, and the demand for flame-retardancy is increasing day by day.

For the past flame retardants for polyester fibers, halogen compounds have been mainly used with the most notable example of hexabromocyclododecane (HBCD). However, these compounds have been regulated more and more as being considered as substances having low degradability and high bioaccumulation potential. In addition, since products with flame proof finish will produce toxic hydrogen halide when being burned, development of safer flame retardants is desired. As a result, researches for phosphorus compounds not containing halogens are eagerly conducted for flame retardants for polyester fibers.

The following prior arts exist for a flame retardant for polyester fibers, consisting of a phosphorus compound that does not contain halogen, and a flame retarding method using the flame retardant.

Japanese Laid-Open Publication No. 2002-275473 (Patent Document 1) discloses a phosphorus compound having a dibenzoxaphosphorineoxide backbone, and both Japanese Laid-Open Publication No. 2000-328445 (Patent Document 2) and Japanese Laid-Open Publication No. 2003-27373 (Patent Document 3) disclose resorcinol bis-diphenylphosphate (RPD). While these compounds have high flame retardancy, they also have defects in their physical properties, such as light resistance, durability and stainability.

As a compound for overcoming such problems, Domestic Publication of PCT International Publication WO 2007/032277 (Patent Document 4) discloses 5,5-dimethyl-2-(2'-phenylphenoxy)-1,3,2-dioxaphosphorin ane-2-oxide as a phosphorus compound. This compound is excellent in hydrolysis resistance and heat resistance, and thus, the compound has excellent preservation stability when used as a flame proof finish agent, and it can provide high flame retardancy without reducing the physical properties of resin or fiber. The compound also has high adherence and exhaustion properties to polyester fibers and does not prevent a dye from adhering to the fibers. Thus, the compound is an extremely excellent phosphorus compound which allows fibers after flame retardant dying treatment to have excellent light resistance, durability and rubbing fastness.

For the method for synthesizing the compounds described above, the following method is generally known.

Patent Document 4 describes a synthesizing method, in which a phenol compound or naphthol compound, which may be substituted with di-substituted phosphorohalidate, are allowed to react in the presence of triethylamine as a hydrogen halide scavenger, and, if needed, a Lewis acid catalyst such as magnesium chloride, to synthesize a corresponding phosphate.

However, with this method, it is difficult to perform synthesis with favorable purity, and the method requires recrystallization to increase the purity. Furthermore, since an expensive amine compound, such as triethylamine, tributylamine or pyridine, is used as a hydrogen halide scavenger, the raw material cost drastically increases. Furthermore, since hydrogen halide salt of the amine compound is produced as a by-product during the reaction, causing the stirring effect to decrease, a larger amount of a reaction solvent is necessary. Furthermore, filtration and water treatment are known as publicly known techniques for removing hydrogen halide salt of the amine compound after capturing the hydrogen halide. However, through filtration, a large amount of the objective substance, i.e., phosphoric acid ester, will remain in the hydrogen halide salt of the amine compound, and the device for handling the filtration will be large-scale. Thus, water treatment is considered for industrial purposes. However, a large amount of water will be required for the water treatment, which greatly reduces the capacity efficiency in the production. Moreover, since the water layer during the removal of hydrogen halide salt of the amine compound contains a large amount of organic amine salt, the product is likely to be contaminated by organic material, which will cause reduction in the yield. Moreover, in the step of recovering amine from amine salt water, a large amount of strong alkali aqueous solution, such as sodium hydroxide or potassium hydroxide, is required to isolate amines, which will further increase the cost. Furthermore, the aqueous solution after recovering the amine has high concentration of alkali metal salt, and it is difficult for ordinary facilities to perform waste water treatment due to a small amount of remaining amine. Furthermore, the amine after being recovered contains water, which will require dehydrating, distilling or other steps.

As described above, the use of an amine compound for reaction has the defects of, not only causing the increase in the raw material cost, but also requiring auxiliaries or the like for recovery and purification. Furthermore, water containing high concentration of hydrogen halide salt of the amine compound cannot be disposed of through ordinary methods from the environmental point of view, and thus, a special treatment will be necessary for the waste water treatment. As such, from the cost, facilities, labor and various other points of view, it is extremely disadvantageous to apply reactions using an amine compound for industrial purposes.

CITATION LIST

Patent Document

[Patent Document 1] Japanese Laid-Open Publication No. 2002-275473

[Patent Document 2] Japanese Laid-Open Publication No. 2000-328445

[Patent Document 3] Japanese Laid-Open Publication No. 2003-27373
[Patent Document 4] Domestic Publication of PCT International Publication WO 2007/032277

DISCLOSURE OF INVENTION

Technical Problem

It is an objective of the present invention to provide a novel production method which enables to obtain a phosphorus compound having both a aromatic substituent and a phosphorinane backbone, by allowing the phosphorus compound to react in the presence of only metal halide, without using an expensive hydrogen halide scavenger, such as triethylamine, tributylamine or pyridine, without going through a complicated post treatment step or a step of recovering a solvent, and with a more favorable yield and purity compared to conventional methods.

Solution to Problem

As a result of researches eagerly conducted by the inventors to achieve the objective described above, it has been found that the objective described above can be achieved by the following method, and the present invention has been completed based on the finding.

Specifically, according to the present invention, the following methods are provided.

(Item 1)

A method for producing a phosphoric acid ester, comprising:

a step (1):

a step of allowing phosphorus oxytrihalide represented by Formula (I)

[Chemical Formula 1]

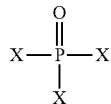

(I)

(wherein X is halogen)
to react with a phenol compound or naphthol compound represented by Formula (II)
[Chemical Formula 2]

(II)

(wherein $R^1$, $R^2$, $R^3$, $R^4$ and $R^5$ are independent from one another, and are a hydrogen atom, a straight or branched-chain $C_{1-6}$ alkyl group, or a $C_{6-12}$ aryl group which may be substituted with a straight or branched-chain $C_{1-4}$ alkyl group, and alternatively $R^1$ and $R^2$, $R^2$ and $R^3$, $R^3$ and $R^4$, or $R^4$ and $R^5$ may form a 6-membered ring together with the carbon atoms of the benzene ring to which these groups are bound, provided that $R^1$, $R^2$, $R^3$, $R^4$ and $R^5$ are not hydrogen atoms at the same time), at a molar ratio of 1.1-3.0:1 in the presence of a metal halide, to produce a mono-substituted phosphorodihalidate represented by Formula (III)
[Chemical Formula 3]

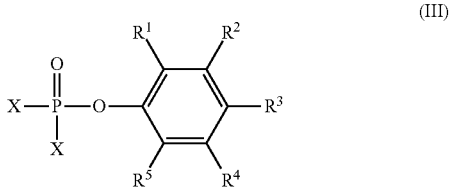

(wherein X, $R^1$, $R^2$, $R^3$, $R^4$ and $R^5$ have the same meaning as the above-described meaning); and a step (2):

a step of allowing the mono-substituted phosphorodihalidate obtained in the step (1) represented by the Formula (III)
[Chemical Formula 4]

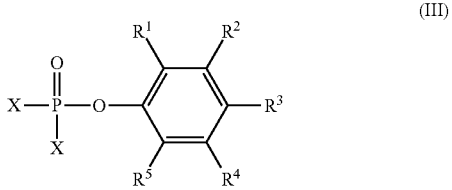

(wherein X, $R^1$, $R^2$, $R^3$, $R^4$ and $R^5$ have the same meaning as the above-described meaning)
to react with a diol compound represented by Formula (IV)
[Chemical Formula 5]

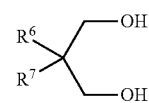

(IV)

(wherein $R^6$ and $R^7$ are independent from each other, and are a hydrogen atom, a straight or branched-chain $C_{1-6}$ alkyl group, or a $C_{6-12}$ aryl group which may be substituted with a straight or branched-chain $C_{1-4}$ alkyl group) so as to perform a dehydrohalogenation reaction to produce a phosphorus compound represented by Formula (V)
[Chemical Formula 6]

(V)

(wherein $R^1$, $R^2$, $R^3$, $R^4$, $R^5$, $R^6$ and $R^7$ have the same meaning as the above-described meaning).

(Item 2)

The method for producing a phosphoric acid ester according to item 1, wherein the ratio of the amount of the diol, represented by the Formula (IV), used in the step (2) is 0.90 to 0.99 molar equivalent based on 1 mole of a halogen atom of the mono-substituted phosphorodihalidate represented by the Formula (III).

(Item 3)

The method for producing a phosphoric acid ester according to item 1 or 2, wherein the metal halide in the step (1) is magnesium chloride and/or aluminum chloride.

(Item 4)

The method for producing a phosphoric acid ester according to any of items 1 to 3, wherein the reaction in the step (1) is performed at a reaction temperature of 80° C. to 140° C.

(Item 5)

The method for producing a phosphoric acid ester according to any of items 1 to 4, wherein the step (1) comprises a step of removing unreacted phosphorus oxytrihalide after the reaction between the phosphorus oxytrihalide and the phenol compound or naphthol compound.

(Item 6)

The method for producing a phosphoric acid ester according to item 5, wherein the removal of the unreacted phosphorus oxytrihalide in the step (1) is performed at a temperature of 80° C. to 140° C. and under a reduced pressure of 20 kPa or less.

(Item 7)

The method for producing a phosphoric acid ester according to any of items 1 to 6, wherein the reaction in the step (2) is performed at a reaction temperature of 70° C. to 160° C.

(Item 8)

The method for producing a phosphoric acid ester according to any of items 1 to 7, wherein in the step (2), a solvent is used in an amount of 0.5 to 6 fold by weight to that of the diol represented by the Formula (IV), and the solvent is one or more solvents selected from the group consisting of toluene, xylene, chlorobenzene, and o-dichlorobenzene.

(Item 9)

The method for producing a phosphoric acid ester according to any of items 1 to 8, further comprising a step of purifying the phosphoric acid ester represented by the Formula (V) obtained in the step (2), wherein at least one type of treatment is selected from the group consisting of acid washing, alkaline washing, water washing, reduced pressure distillation, and recrystallization.

(Item 10)

The method for producing a phosphoric acid ester according to any of items 1 to 8, further comprising a step of removing impurities in the phosphoric acid ester represented by the Formula (V) obtained in the step (2), at a temperature of 70° C. to 160° C. and under a reduced pressure of 20 kPa or lower.

(Item 11)

The method for producing a phosphoric acid ester according to any of items 1 to 10, wherein the phosphorus oxytrihalide represented by the Formula (I) in the step (1) is phosphorus oxychloride or phosphorus oxybromide.

(Item 12)

The method for producing a phosphoric acid ester according to any of items 1 to 11, wherein the phenol compound or naphthol compound represented by the Formula (II) in the step (1) is 2-hydroxybiphenyl.

(Item 13)

The method for producing a phosphoric acid ester according to any of items 1 to 12, wherein the diol compound represented by the Formula (IV) in the step (2) is 2,2-dimethyl-1,3-propanediol.

Advantageous Effects of Invention

According to the present invention, a phosphorus compound having both an aromatic substituent and a phosphorinane backbone can be produced by allowing the phosphorus compound to react in the presence of only metal halide, without using an expensive hydrogen halide scavenger, such as triethylamine, tributylamine or pyridine, without going through a complicated post treatment step or a step of recovering a solvent, and with a lower cost and a more favorable purity and yield compared to conventional methods.

BEST MODE FOR CARRYING OUT THE INVENTION

The method for producing a phosphoric acid ester according to the present invention comprises a step (1) and a step (2) as follows.

(Step (1))

The step (1) is a step of allowing phosphorus oxytrihalide represented by a Formula (I)

[Chemical Formula 7]

(wherein X is halogen)

to react with a phenol compound or naphthol compound represented by Formula (II)

[Chemical Formula 8]

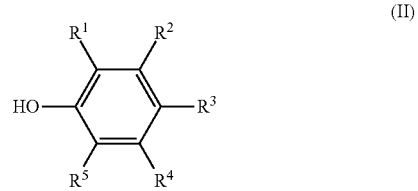

(wherein $R^1$, $R^2$, $R^3$, $R^4$ and $R^5$ are independent from one another, and are a hydrogen atom, a straight or branched-chain $C_{1-6}$ alkyl group, or a $C_{6-12}$ aryl group which may be substituted with a straight or branched-chain $C_{1-4}$ alkyl group, and alternatively $R^1$ and $R^2$, $R^2$ and $R^3$, $R^3$ and $R^4$, or $R^4$ and $R^5$ may form a 6-membered ring together with the carbon atoms of the benzene ring to which these groups are bound, provided that $R^1$, $R^2$, $R^3$, $R^4$ and $R^5$ are not hydrogen atoms at the same time) to produce a mono-substituted phosphorodihalidate represented by Formula (III).

[Chemical Formula 9]

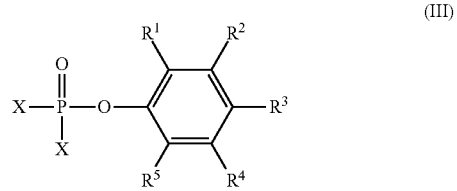

(wherein X, $R^1$, $R^2$, $R^3$, $R^4$ and $R^5$ have the same meaning as the above-described meaning) This is represented by a reaction formula, as follows.

[Chemical Formula 10]

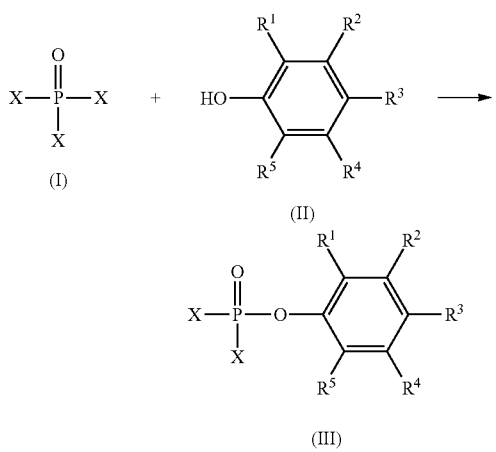

(Characteristics of the Formula (I))

X in the Formula (I) in the step (1) is a halogen atom, including fluorine, chlorine, bromine and iodine, for example. The three Xs may be identical with, or different from, one another, but in one embodiment, it is preferable to define the three Xs as being identical in terms of the ease for synthesizing the compound of the Formula (I).

It is preferable for X to be bromine or chlorine since it is easy to obtain the raw material and it is easy to perform the synthesis as will be described later. Chlorine is more preferable.

The compound of the Formula (I) specifically includes phosphorus oxychloride and phosphorus oxybromide, either of which can be used. Phosphorus oxychloride is particularly preferable in terms of availability and cost.

(Characteristics of the Formula (II))

$R^1$, $R^2$, $R^3$, $R^4$ and $R^5$ in the Formula (II) are independent from one another, and are a hydrogen atom, a straight or branched-chain $C_{1-6}$ alkyl group, or a $C_{6-12}$ aryl group which may be substituted with a straight or branched-chain $C_{1-4}$ alkyl group, and alternatively $R^1$ and $R^2$, $R^2$ and $R^3$, $R^3$ and $R^4$, or $R^4$ and $R^5$ may form a 6-membered ring together with the carbon atoms of the benzene ring to which these groups bound, provided that not all of $R^1$, $R^2$, $R^3$, $R^4$ and $R^5$ are hydrogen atoms at the same time.

In a preferred embodiment, $R^1$, $R^2$, $R^3$, $R^4$ and $R^5$ in the Formula (II) are independent from one another, and are a hydrogen atom, a straight or branched-chain $C_{1-6}$ alkyl group, or a $C_{6-12}$ aryl group which may be substituted with a straight or branched-chain $C_{1-4}$ alkyl group, and alternatively $R^1$ and $R^2$, $R^2$ and $R^3$, $R^3$ and $R^4$, or $R^4$ and $R^5$ may form a 6-membered ring together with the carbon atoms of the benzene ring to which these groups are bound, provided that not all of $R^1$, $R^2$, $R^3$, $R^4$ and $R^5$ are hydrogen atoms at the same time in this embodiment.

In a still preferred embodiment, $R^1$, $R^2$, $R^3$, $R^4$ and $R^5$ in the Formula (II) are independent from one another, and are a hydrogen atom, or a $C_{6-12}$ aryl group which may be substituted with a straight or branched-chain $C_{1-4}$ alkyl group, provided that not all of $R^1$, $R^2$, $R^3$, $R^4$ and $R^5$ are hydrogen atoms at the same time in this embodiment.

As described above, not all of $R^1$, $R^2$, $R^3$, $R^4$ and $R^5$ are hydrogen atoms at the same time in the compound of the Formula (II). Thus, the compound of the Formula (II) is not unsubstituted phenol. Specifically, one to four of $R^1$, $R^2$, $R^3$, $R^4$ and $R^5$ are hydrogen atoms. Preferably, two to four of $R^1$, $R^2$, $R^3$, $R^4$ and $R^5$ are hydrogen atoms. Still preferably, three or four of $R^1$, $R^2$, $R^3$, $R^4$ and $R^5$ are hydrogen atoms. Still preferably, four of $R^1$, $R^2$, $R^3$, $R^4$ and $R^5$ are hydrogen atoms. In addition, it is preferable for $R^1$ or $R^5$ not to be hydrogen. That is, it is preferable for $R^2$, $R^3$ and $R^4$ to be hydrogen.

In the present specification, the term "may be substituted" means either having a substituent or not having a substituent. For example, an alkyl group that may be substituted means a substituted alkyl or non-substituted alkyl group. An aryl group that may be substituted means a substituted aryl or non-substituted aryl group.

When $R^1$, $R^2$, $R^3$, $R^4$ and $R^5$ are "a straight or branched-chain $C_{1-6}$ alkyl group", the carbon number of the alkyl group may be any of 1, 2, 3, 4, 5 or 6. Specific examples of the straight-chain alkyl group include a methyl group, an ethyl group, a n-propyl group, a n-butyl group, a n-pentyl group, and a n-hexyl group. Specific examples of the branched-chain alkyl group include an isopropyl group, an isobutyl group, a sec-butyl group, and a tert-butyl group.

When $R^1$, $R^2$, $R^3$, $R^4$ and $R^5$ are "a $C_{6-12}$ aryl group which may be substituted with a straight or branched-chain $C_{1-4}$ alkyl group", the specific examples of the "aryl group" include a phenyl group, a 1-naphthyl group, and a 2-naphthyl group. The carbon number of the alkyl group in the "straight or branched-chain $C_{1-4}$ alkyl group", which may be introduced as a substituent onto an aryl group, may be any of 1, 2, 3 or 4. Specific examples of the straight-chain alkyl group include a methyl group, an ethyl group, a n-propyl group, and a n-butyl group. Specific examples of the branched-chain alkyl group include an isopropyl group, an isobutyl group, a sec-butyl group, and a tert-butyl group.

Due to the availability of the compound of Formula (II) and the high exhaustion properties to fibers when the phosphorus compound of the Formula (V) is used as a flame retardant for polyester fibers, it is preferable that any one of $R^1$, $R^2$, $R^3$, $R^4$ and $R^5$ is an unsubstituted aryl group and the rest of them are hydrogen atoms. It is more preferable for any one of $R^1$, $R^3$, and $R^5$ to be a phenyl group. It is even more preferable for either of $R^1$ or $R^5$ to be a phenyl group.

When the compound of the Formula (II) is a substituted phenol compound, position 2 of the phenol compound is preferably substituted. When there exists a substituent at position 2 of the phenol, the reactivity of the phenol typically tends to be decreased due to its steric hindrance. However, according to the method of the present invention, a favorable reactivity is maintained and thus the present invention is advantageous. Specific examples of the phenol compound that may be substituted include 2-hydroxybiphenyl, 3-hydroxybiphenyl, 4-hydroxybiphenyl and 2,6-diphenylphenol. Herein, it is preferable for the phenol to have one or more substituents. It is preferable for a substituent to be present at the position 2 of the phenol.

When the compound of the Formula (II) is a naphthol compound that may be substituted, specific examples thereof include 1-naphthol and 2-naphthol. Among them, from the viewpoint of availability and the cost, and also from the viewpoint that the exhaustion properties to fibers increase when a phosphorus compound is used as a flame retardant for polyester fibers, 2-hydroxybiphenyl, 3-hydroxybiphenyl, 4-hydroxybiphenyl, 1-naphthol and 2-naphthol are preferable. 2-hydroxybiphenyl, 4-hydroxybiphenyl, and 2-naphthol are more preferable. 2-hydroxybiphenyl is even more preferable.

(Catalyst)

The reaction in the step (1) is performed in the presence of a metal halide. A metal halide having Lewis acidity is preferable.

In the step (1), the metal halide acts as a catalyst. The metal in the metal halide may be any metal, including alkali metal, alkaline earth metal, transition metal and the like. Preferable examples of the metal include magnesium, aluminum, zinc, titanium and boron. The halogen in the metal halide may be any halogen, and specific examples of the halogen include fluorine, chlorine, bromine and iodine. Specific examples of the metal halide include magnesium chloride, aluminum chloride, zinc chloride, titanium tetrachloride, and boron trifluoride ether complex. Further, two or more of these types of metal halide may be mixed and used. For the reaction described above, it is particularly preferable to use magnesium chloride as a catalyst in terms of its reactivity and handling.

(Amount of Catalyst Used)

The amount of the metal halide used in the step (1) is not particularly limited. The amount of the metal halide is preferably 0.001 mol or more to 1 mol of the phenol compound or naphthol compound, i.e., the compound of the Formula (II). More preferably, the amount is 0.005 mol or more to 1 mol of the phenol compound or naphthol compound. Even more preferably, the amount is 0.008 mol or more to 1 mol of the phenol compound or naphthol compound. Particularly preferably, the amount is 0.009 mol or more to 1 mol of the phenol compound or naphthol compound. Furthermore, preferably, the amount is 0.1 mol or less to 1 mol of the phenol compound or naphthol compound. More preferably, the amount is 0.05 mol or less. Even more preferably, the amount is 0.02 mol or less to 1 mol of the phenol compound or naphthol compound. Particularly preferably, the amount is 0.015 mol or less to 1 mol of the phenol compound or naphthol compound. If the amount of the catalyst used is too little, then the reactivity will be decreased and the reaction needs to be made at a higher temperature. Thus, the purity of mono-substituted phosphorodihalidate (Formula (III)) will be significantly reduced. In addition, if the amount of the catalyst used is too much, then the reaction will be rapidly accelerated, which makes it difficult to control the reaction.

(Excess Ratio of Phosphorus Oxytrihalide)

The ratio of the amount of phosphorus oxytrihalide (Formula (I)) used in the reaction of the step (1) is between 1.1 mol or more and 3.0 mol or less to 1 mol of the phenol compound or naphthol compound (i.e., the compound of the Formula (II)).

If the ratio of the amount of phosphorus oxytrihalide used is too small, for example, if the ratio is below 1.1 mol to 1 mol of the phenol compound or naphthol compound, then the purity of mono-substituted phosphorodihalidate obtained (Formula (III)) will significantly drop. It will result in the hydrolysis resistance and heat resistance to deteriorate and the flame retardancy to be poor. Therefore, this is not preferable. In addition, if the ratio of the amount of phosphorus oxytrihalide used exceeds 3 mol to 1 mol of the phenol compound or naphthol compound, then not only the purity of the corresponding mono-substituted phosphorodihalidate obtained (Formula (III)) will not be largely different, but it will also mean that a large amount of phosphorus oxytrihalide was used in vain. Specifically, the ratio of the amount of phosphorus oxytrihalide used may be 1.2 mol or more, 1.3 mol or more, or 1.4 mol or more, to 1 mol of a phenol compound or naphthol compound. Preferably, the amount of phosphorus oxytrihalide used is 1.5 mol or more to 1 mol of the phenol compound or naphthol compound. It is also possible to set the amount to be 1.6 mol or more, 1.7 mol or more, 1.8 mol or more, or 1.9 mol or more to 1 mol of the phenol compound or naphthol compound. The amount of 2.0 mol or more to 1 mol of the phenol compound or naphthol compound is particularly preferable. In addition, it is also possible to set the amount to be 2.1 mol or more or 2.2 mol or more to 1 mol of the phenol compound or naphthol compound as the need arises. The ratio of the amount of phosphorus oxytrihalide is preferably 2.9 mol or less to 1 mol of the phenol compound or naphthol compound. More preferably, the ratio is 2.8 mol or less. Even more preferably, the ratio is 2.7 mol or less, and still even more preferably, 2.6 mol or less, and particularly preferably 2.5 mol or less to 1 mol of the phenol compound or naphthol compound. In addition, it is also possible to set the ratio to be 2.4 mol or less or 2.3 mol or less to 1 mol of the phenol compound or naphthol compound as needs arise.

(Reaction Temperature)

The reaction temperature in the step (1) is not particularly limited. The reaction temperature in the step (1) is preferably 80° C. or higher, more preferably 85° C. or higher, even more preferably 90° C. or higher, and particularly preferably 95° C. or higher. In addition, the reaction temperature in the step (1) is preferably 140° C. or lower, more preferably 130° C. or lower, even more preferably 120° C. or lower, and still even more preferably 115° C. or lower. In addition, it is possible to set the reaction temperature to be 110° C. or lower, and the reaction temperature is particularly preferably 105° C. or lower. If the reaction temperature is too low, then the reactivity will drop, which is not preferable. On the other hand, if the reaction temperature is too high, then di-substituted phosphorohalidate, tri-substituted phosphate or the like will be produced as a by-product, other than mono-substituted phosphorodihalidate obtained (Formula (III)), and the purity will drop, which is not preferable.

It is possible to set the reaction time in the step (1) as appropriate in consideration of conditions such as a reaction temperature. The reaction time is preferably 15 minutes or more, more preferably 30 minutes or more, and even more preferably 1 hour or more. In addition, the reaction time is preferably 1 day or less, more preferably 12 hours or less, and even more preferably 5 hours or less. It is also possible to set the reaction time to be 3 hours or less, 2 hours or less, or 1 hour and a half hours or less.

(Atmosphere)

The reaction in the step (1) may be performed under the normal atmosphere. However, for the purpose of moisture prevention, it is preferable to perform the reaction under the atmosphere of inert gas such as nitrogen gas.

(Recovery of Phosphorus Oxytrihalide)

After the reaction in the step (1), unreacted phosphorus oxytrihalide is removed as the need arises. For the specific removing method, an easy and preferable method is distillation under a reduced pressure to remove such unreacted phosphorus oxytrihalide as a low boiling point component. Although the temperature for the reduced pressure distillation is not particularly limited, it is preferably 80° C. or higher. More preferably, the temperature is 85° C. or higher. Even more preferably, the temperature is 90° C. or higher, and particularly preferably, the temperature is 95° C. or higher. In addition, the temperature is preferably 140° C. or lower, more preferably 130° C. or lower, even more preferably 120° C. or lower, still even more preferably 110° C. or lower, and particularly preferably 105° C. or lower. The pressure is preferably 20 kPa or less, more preferably 15 kPa or less, even more preferably 10 kPa or less, and particularly preferably 8 kPa or less. Although the lower limit of the pressure is not particularly defined, it is possible to use a pressure of 1 kPa or more, 3 kPa or more, or 5 kPa or more, if there is a restriction in terms of the cost of the facilities or the like.

The removed phosphorus oxytrihalide can be recovered and reused as a material for the next reaction. In the case of being reused, the phosphorus oxytrihalide recovered can also be reused as a material for the next reaction in the state as it was recovered without conducting further treatment (e.g., purification).

If the step (2) is performed while phosphorus oxytrihalide remains in the reaction system, the phosphorus oxytrihalide will react with the diol compound during the reaction in the step (2) and the purity of the objective substance (Formula (V)) will drop, which is not preferable.

(Reaction Solvent)

The reaction in the step (1) can normally be performed without using a solvent. However, it is also possible to use a solvent that is inert to the reaction, as the need arises. Usable solvents include, for example, the following: hydrocarbon-type solvents such as hexane, cyclohexane, heptane, octane, benzene, toluene, xylene and petroleum spirit;

halogen-containing hydrocarbon-type solvents such as chloroform, carbon tetrachloride, dichloromethane, dichloroethane, trichloroethane, tetrachloroethane, chlorobenzene, chlorotoluene and o-dichlorobenzene; and ether-type solvent such as diisopropylether, dibutylether, 1,4-dioxane, ethyleneglycoldimethylether, diethyleneglycoldimethylether, triethyleneglycoldimethylether or polyethyleneglycoldimethylether whose number of ethyleneglycol repeating units is more than 3, and ethyleneglycoldiethylether.

(Step (2))

In the step (2), the mono-substituted phosphorodihalidate obtained in the step (1) and represented by Formula (III)

[Chemical Formula 11]

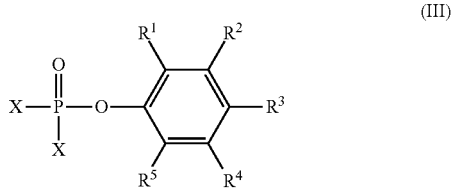

(III)

(wherein X, $R^1$, $R^2$, $R^3$, $R^4$ and $R^5$ have the same meaning as the above-described meaning) is allowed to react with the diol compound represented by the Formula (IV).

[Chemical Formula 12]

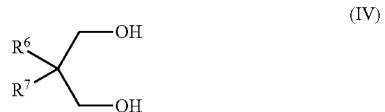

(IV)

(wherein $R^6$ and $R^7$ are independent from each other, and are a hydrogen atom, a straight or branched-chain $C_{1-6}$ alkyl group, or a $C_{6-12}$ aryl group which may be substituted with a straight or branched-chain $C_{1-4}$ alkyl group) In this step, a dehydrohalogenation reaction is performed between the compound of the Formula (III) and the compound of the Formula (IV). Then, a phosphorus compound represented by the Formula (V) will be obtained.

[Chemical Formula 13]

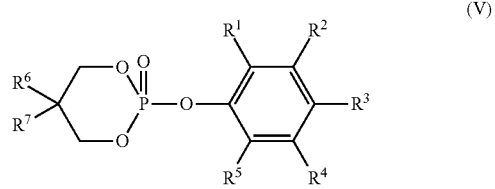

(V)

(wherein $R^1$, $R^2$, $R^3$, $R^4$, $R^5$, $R^6$ and $R^7$ have the same meaning as the above-described meaning)

The following is a representation of this reaction.

[Chemical Formula 14]

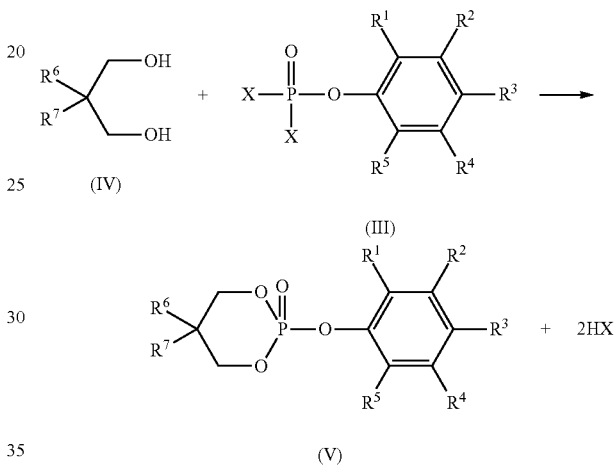

(Characteristics of Formula (IV))

$R^6$ and $R^7$ in the Formula (IV) in the step (2) are independent from each other, and are a hydrogen atom, a straight or branched-chain $C_{1-6}$ alkyl group, or a $C_{6-12}$ aryl group which may be substituted with a straight or branched-chain $C_{1-4}$ alkyl group.

The "straight or branched-chain $C_{1-6}$ alkyl group" and/or "$C_{6-12}$ aryl group which may be substituted with a straight or branched-chain $C_{1-4}$ alkyl group" in $R^6$ and $R^7$ include the above-described substituents defined in relation to $R^1$, $R^2$, $R^3$, $R^4$ and $R^5$.

For the combination of $R^6$ and $R^7$, it is preferable that both of $R^6$ and $R^7$ are a straight or branched-chain $C_{1-6}$ alkyl group since it is easy to obtain the raw material and it is easy to perform the synthesis as will be described later. It is more preferable that both of $R^6$ and $R^7$ are a straight-chain $C_{1-6}$ alkyl group. It is even more preferable that both of $R^6$ and $R^7$ are a straight-chain $C_{1-4}$ alkyl group. $R^6$ and $R^7$ are particularly preferably a combination of a methyl group and a methyl group, or a combination of a ethyl group and a n-butyl group.

As the diol compound of the Formula (IV) in the step (2), a diol which is capable of forming a 6-membered ring when being allowed to react with a mono-substituted phosphorodihalidate, i.e., a compound having a structure (HO—C≡C—C—OH) that has three carbon atoms in between two hydroxyl groups, such as 1,3-propanediol, is desirable. Ethanediol, 1,4-butanediol and the like, which form a ring other than a 6-membered ring, are not preferable because they will cause complicated reactions of a cyclization reaction and a crosslinking reaction, an ester exchange reaction or the like, and will produce by-products and high molecular weight components.

Specific examples of propanediol compounds that form a 6-membered ring include 1,3-propanediol, 2,2-dimethyl-1,3-propanediol (neopentyl glycol), 2,2-diethyl-1,3-propanediol, 2-methyl-2-propyl-1,3-propanediol, 2-butyl-2-ethyl-1,3-propanediol, and 2-phenyl-1,3-propanediol. Among them, 1,3-propanediol, 2,2-dimethyl-1,3-propanediol, and 2-butyl-2-ethyl-1,3-propanediol are preferable due to the availability and the cost. 2,2-dimethyl-1,3-propanediol and 2-butyl-2-ethyl-1,3-propanediol are more preferable since the reaction products thereof have high chemical stability, and 2,2-dimethyl-1,3-propanediol is particularly preferable.

In general, when phosphorus oxytrihalide is allowed to react with a phenol compound in the absence of a hydrogen halide scavenger to synthesize a tri-substituted phosphate, the phosphate to be generated will be stable to an acid. However, when phosphorus oxytrihalide is allowed to react with aliphatic alcohol in the absence of a hydrogen halide scavenger to attempt to produce tri-substituted phosphate in accordance with the Formula (A) described below, the phosphate obtained will be unstable to an acid. Thus, such a side reaction as shown in the Formula (B) will occur, and the yield of the objective substance will be largely decreased. Accordingly, it is considered that it is necessary to use a hydrogen halide scavenger when phosphorus oxytrihalide is allowed to react with aliphatic alcohol. Hence, it is a surprising discovery that in producing a tri-substituted phosphate using aliphatic alcohol, an alkylphosphate compound can be obtained at a high yield without a hydrogen halide scavenger, as in the present invention.

[Chemical Formula 15]

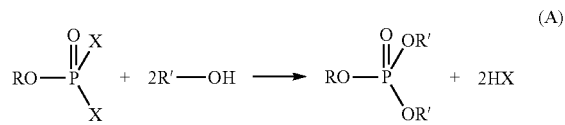

[Chemical Formula 16]

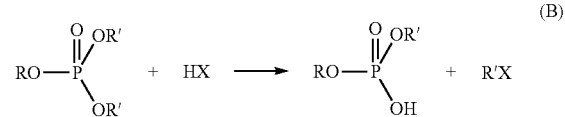

(Excess Ratio of Diol Compound)

The amount of the diol compound (Formula (IV)) used in the reaction in the step (2) is determined with respect to the content of halogen atoms in the mono-substituted phosphorodihalidate (Formula (III)) generated in the step (1).

The measurement of the content of halogen atoms is performed, for example, using the following method. The reaction solution after phosphorus oxytrihalide was removed is dissolved into ethanol and/or water; sodium hydroxide and/or potassium hydroxide are added to make the solution alkaline; and the solution is refluxed for about 30 minutes. The solution is cooled by ice application or the like, and then nitric acid is added to make the solution acidic; and the solution is titrated using a silver nitrate solution; and thereby the content of halogen atoms can be measured.

The ratio of the amount of the diol compound (Formula (IV)) used in the reaction in the step (2) is preferably 0.90 molar equivalent or more based on 1 mole of the halogen atom of the mono-substituted phosphorodihalidate (Formula (III)). The ratio is more preferably 0.91 molar equivalent or more, even more preferably 0.92 molar equivalent or more, and particularly preferably 0.93 weight equivalent or more based on 1 mole of the halogen atom of the mono-substituted phosphorodihalidate (Formula (III)). In addition, the ratio is preferably 0.99 molar equivalent or less, more preferably 0.98 molar equivalent or less, even more preferably 0.97 molar equivalent or less, and particularly preferably 0.96 molar equivalent or less based on 1 mole of the halogen atom of the mono-substituted phosphorodihalidate (Formula (III)). In addition, it is possible to set the ratio to be 0.95 molar equivalent or less based on 1 mole of the halogen atom of the mono-substituted phosphorodihalidate (Formula (III)).

It is noted that in the reaction between the compound of the Formula (III) and the compound of the Formula (IV), 1 mol of the compound of the Formula (III) is allowed to react with 1 mol of the compound of the Formula (IV). Thus, 1 molar equivalent based on 1 mole of the halogen atoms described above corresponds to 1 mol of the compound of the Formula (IV) to 1 mol of the compound of the Formula (III).

If the ratio of the diol compound used is too low with respect to the halogen atoms of the mono-substituted phosphorodihalidate, a large amount of unreacted mono-substituted phosphorodihalidate will remain in the reaction product and it causes a decrease in the yield and an increase in the load of waste water. Therefore it is not preferable. Furthermore, if the ratio of the diol compound used is too high, the diol compound will not form a cyclic structure due to a side reaction such as an ester exchange reaction or a crosslinking reaction. As a result, a dioxaphosphorinane backbone will not be formed, which tends to cause the purity of the objective substance, or the phosphorus compound (Formula (V)), to drop. As a result, the flame retardancy will tend to drop. Thus, in one embodiment, the ratio of the diol compound (Formula (V)) used in the step (2) is preferably 0.90-0.99 molar equivalent, more preferably 0.93-0.97 molar equivalent, and even more preferably 0.93-0.95 molar equivalent.

The reaction in the step (2) can be performed in the presence of an organic solvent.

The organic solvents are not particularly limited as long as they are solvents that are inert to the reaction. Usable organic solvents include the following: hydrocarbon-type solvents such as hexane, cyclohexane, heptane, octane, benzene, toluene, xylene and petroleum spirit; halogen-containing hydrocarbon-type solvents such as chloroform, carbon tetrachloride, dichloromethane, dichloroethane, trichloroethane, tetrachloroethane, chlorobenzene, chlorotoluene and o-dichlorobenzene; and ether-type solvent such as diisopropylether, dibutylether, 1,4-dioxane, ethyleneglycoldimethylether, diethyleneglycoldimethylether, triethyleneglycoldimethylether or polyethyleneglycoldimethylether whose number of ethyleneglycol repeating units is more than 3, and ethyleneglycoldiethylether. Among these solvents, in terms of the easy handling, toluene, xylene, chlorobenzene, and o-dichlorobenzene are preferable. Toluene and chlorobenzene are more preferable, and toluene is particularly preferable.

The amount of the solvent used can be set as appropriate so that the reaction will progress favorably, and there is no particular limitation to the amount. The amount of the solvent is preferably 0.5 fold or higher by weight of the diol compound used, more preferably 1 fold or higher by weight, even more preferably 1.5 fold or higher by weight, and particularly preferably 2 fold or higher by weight. In addition, the amount of the solvent is preferably 6 fold or lower by weight of the diol compound used, more preferably 5 fold or lower by weight, even more preferably 4 fold or lower by weight, and particularly preferably 3 fold or lower by weight of the diol compound.

In addition, in the step (2), the mono-substituted phosphorodihalidate may be added into a mixture of the diol compound (Formula (IV)) and a solvent, or alternatively the diol compound (Formula (IV)) may be added into a mixture of mono-substituted phosphorodihalidate and a solvent; however, the latter is preferable in terms of the reactivity, purity of the objective compound, and the like.

(Temperature)

The reaction temperature in the step (2) is preferably 70° C. or higher, more preferably 75° C. or higher, even more preferably 80° C. or higher, and still even more preferably 85° C. or higher. The reaction temperature is particularly preferably 90° C. or higher. In addition, the reaction temperature is preferably 160° C. or lower, more preferably 150° C. or lower, even more preferably 140° C. or lower, still even more preferably 130° C. or lower, yet still even more preferably 120° C. or lower, particularly preferably 110° C. or lower, and most preferably 105° C. or lower. If the reaction temperature is too low, then the reactivity will drop, which is not preferable. In addition, if the reaction temperature is too high, then side reactions will be apt to occur and the purity of the objective substance (Formula (V)) will be decreased, which is not preferable.

(Reaction Time)

The reaction time in the step (2) can be set as appropriate depending on conditions such as a reaction temperature. The reaction time is preferably 30 minutes or more, and more preferably 1 hour or more. In addition, the reaction time is preferably 12 hours or less, and more preferably 6 hours or less.

(Atmosphere)

The reaction in the step (2) may be performed under the normal atmosphere. However, for the purpose of moisture prevention, it is preferable to perform the reaction under the atmosphere of inert gas such as nitrogen gas.

Also, in the reaction in the step (2), hydrogen halide produced as a by-product is removed as the need arises. Specifically, it is preferable to remove hydrogen chloride that is generated (produced as a byproduct) using, for example, a method for reducing pressure inside the system or for blowing inert gas, such as nitrogen gas, into the system.

(Post Treatment Conditions)

In the reacted mixture in the step (2), since impurities such as the raw material, unreacted substance and acidic components remain in the phosphoric acid ester of the Formula (V), it is preferable to perform a step of removing such impurities, as the need arises. For example, the step of removing includes acid washing, alkaline washing, water washing, reduced pressure distillation, recrystallization and the like.

In addition, a solvent may be added as the need arises in the post treatment in order to prevent layer separation properties and crystal deposition. In such a case, the solvent used may be a reaction solvent that was used in the reaction, but it will not be problematic to use other solvents.

When a solvent is used, the amount of the solvent is preferably 1 fold or higher by weight, more preferably 2 fold or higher by weight, even more preferably 3 fold or higher by weight, of the diol compound used in the step (2). In addition, the amount of the solvent is preferably 6 fold or lower by weight, more preferably 5 fold or lower by weight, and even more preferably 4 fold or lower by weight, of the diol compound used.

By acid washing, metal components in the reaction product can be removed. Specifically, aqueous acidic solution, for example, hydrochloric acid, sulfuric acid, phosphoric acid, nitric acid, oxalic acid, or citric acid (e.g., 0.5%-5% aqueous hydrochloric acid or 0.5%-5% aqueous oxalic acid) may be used to wash the obtained reaction product.

By alkaline washing, acidic components in the reaction product can be removed. Specifically, aqueous alkaline solution, for example, sodium hydroxide, potassium hydroxide, calcium hydroxide, sodium carbonate, or sodium hydrogencarbonate (e.g., 1%-5% aqueous sodium hydroxide solution or 1%-10% aqueous sodium carbonate solution) may be used to wash the obtained reaction product.

The reduced pressure distillation for removing impurities such as low boiling point components includes, for example, steam distillation. The temperature for steam distillation is preferably 70° C. or higher, more preferably 80° C. or higher, and even more preferably 100° C. or higher. In addition, the temperature for steam distillation is preferably 160° C. or lower, more preferably 150° C. or lower, and even more preferably 140° C. or lower. The pressure is preferably 20 kPa or less, more preferably 15 kPa or less, and even more preferably 10 kPa or less. Although there is no limitation to the lower limit of the pressure, the pressure of 1 kPa or more, 3 kPa or more or 5 kPa or more can be used in a case where there is a restriction in terms of the cost of the facilities or the like.

In addition, recrystallization may be performed as a method for obtaining a reaction product more easily and at a higher purity. In such a case, any solvent can be used. For example, a solvent such as ethanol, propanol, butanol, toluene, xylene, chlorobenzene, or o-dichlorobenzene may be used to re-crystallize the obtained reacted mixture.

(Conclusion)

As described above, the present invention is exemplified by the use of its preferred embodiments. However, the present invention should not be interpreted solely based on embodiments described above. It is understood that the scope of the present invention should be interpreted solely based on the claims. It is also understood that those skilled in the art can implement equivalent scope of technology, based on the description of the present invention and common knowledge from the description of the detailed preferred embodiments of the present invention. Furthermore, it is understood that any patent, any patent application and any references cited in the present specification should be incorporated by reference into the present specification in the same manner as the contents are specifically described herein.

EXAMPLES

The present invention will be described in further detail using examples and comparative examples; however, the scope of the present invention will not be limited by these examples.

Example 1

Step 1

A four-necked 1-liter flask, equipped with a stirrer, a thermometer, and a reflux condenser, was filled with 170.2 g (1 mol) of 2-hydroxybiphenyl, 337.3 g (2.2 mol) of phosphorus oxychloride and 0.95 g (0.01 mol) of anhydrous magnesium chloride. This mixed liquid was heated to the temperature of 105° C. over three hours while being stirred under a nitrogen atmosphere, and it was stirred for 1 hour at the same temperature (105° C.) to allow a reaction to proceed. After the reaction, the pressure was reduced to 6.7 kPa at a liquid temperature of 105° C. The same pressure was maintained for 1 hour and excess (unreacted) phosphorus oxychloride was recovered. Thus, 290.8 g of 2-biphenylylphosphorodichloridate (chlorine content: 24.7%) was obtained.

Step 2

Next, a four-necked 2-liter flask, equipped with a stirrer, a thermometer, a dropping funnel, and a reflux condenser, was filled with 98.9 g of 2,2-dimethyl-1,3-propanediol (0.95 mol, 0.94 molar equivalent based on 1 mole of halogen atoms of the phosphorodichloridate) and 197.8 g of toluene. This mixed liquid was heated up to 90° C. over 1 hour while being stirred under a nitrogen atmosphere, and then 290.8 g of the 2-biphenylylphosphorodichloridate obtained in the step 1 was added at 90° C. over 2 hours. Thereafter, the mixed liquid was heated to 105° C. over 1 hour, and it was stirred for 1 hour at the same temperature (105° C.) to allow a reaction to proceed. After the reaction, the reaction was continued for 3 hours under a reduced pressure (40.2 kPa) at the same temperature (105° C.) while refluxing toluene.

Thereafter, the reaction solution was cooled down to 90° C. Nitrogen was then introduced to set the pressure inside the flasks normal, and 336 g of toluene was added. At the same temperature (90° C.), washing was performed successively with 200 g of 1.4% aqueous oxalic acid solution and 200 g of 2.3% aqueous sodium carbonate solution, and washing with 200 g of water was performed in the end. Furthermore, steam distillation was performed at 140° C. under a reduced pressure (2.7 kPa) to remove low boiling point components from the reaction product. Thus, 287.8 g (LC purity: 98.5%) of a white solid of 5,5-dimethyl-2-(2'-phenylphenoxy)-1,3,2-dioxaphosphorin ane-2-oxide was obtained. Assuming all the solid was the objective compound, the yield was 95.2%.

Example 2

Step 1

2-biphenylylphosphorodichloridate was obtained in a similar manner as the step 1 in Example 1.

Step 2

Next, a four-necked 2-liter flask, equipped with a stirrer, a thermometer, a dropping funnel, and a reflux condenser, was filled with 98.9 g of 2,2-dimethyl-1,3-propanediol (0.95 mol, 0.94 molar equivalent based on 1 mole of halogen atoms of the phosphorodichloridate) and 197.8 g of toluene. This mixed liquid was heated up to 75° C. over 1 hour while being stirred under a nitrogen atmosphere, and then 290.8 g of the 2-biphenylylphosphorodichloridate obtained in the step 1 was added over 2 hours. Thereafter, the mixed liquid was stirred at the same temperature (75° C.) for 1 hour to allow the reaction to proceed. After the reaction, the reaction was continued under a reduced pressure (40.2 kPa) at the same temperature (75° C.) for 6 hours.

After the reaction, treatment was performed under similar conditions as in Example 1 to obtain 282.6 g (LC purity: 98.1%) of a white solid of 5,5-dimethyl-2-(2'-phenylphenoxy)-1,3,2-dioxaphosphorin ane-2-oxide. Assuming all the solid was the objective compound, the yield was 93.5%.

Example 3

Step 1

2-biphenylylphosphorodichloridate was obtained in a similar manner as in the step 1 in Example 1.

Step 2

Next, a four-necked 2-liter flask, equipped with a stirrer, a thermometer, a dropping funnel, and a reflux condenser, was filled with 290.8 g of 2-biphenylylphosphorodichloridate obtained in the step 1 and 197.8 g of toluene. This mixed liquid was heated up to 90° C. over 1 hour while being stirred under a nitrogen atmosphere, and then 98.9 g of 2,2-dimethyl-1,3-propanediol (0.95 mol, 0.94 molar equivalent based on 1 mole of halogen atoms of the phosphorodichloridate) was added over 2 hours. Thereafter, the mixed liquid was heated up to the temperature of 105° C. over 1 hour and was stirred for 1 hour at the same temperature, to allow a reaction to proceed. After the reaction, the reaction was continued for 3 hours under a reduced pressure (40.2 kPa) at the same temperature (105° C.) while refluxing toluene.

Thereafter, the reacted solution was cooled down to 80° C. Nitrogen was then introduced to set the pressure inside the flasks normal, and 336 g of toluene was added. At the same temperature (80° C.), washing was performed successively with 200 g of 1.1% aqueous hydrochloric acid and 200 g of 7% aqueous sodium carbonate solution, and washing with 200 g of water was performed in the end. Furthermore, steam distillation was performed at 140° C. under a reduced pressure (2.7 kPa) to remove low boiling point components from the reaction product. Thus, 288.1 g (LC purity: 98.9%) of a white solid of 5,5-dimethyl-2-(2'-phenylphenoxy)-1,3,2-dioxaphosphorin ane-2-oxide was obtained. Assuming all the solid was the objective compound, the yield was 95.3%.

Comparative Example 1

Reaction

A four-necked 1-liter flask, equippedwith a stirrer, a thermometer, a dropping funnel, a hydrochloric acid recovering device and a reflux condenser, was filled with 104.0 g (1 mol) of 2,2-dimethyl-1,3-propanediol and 114.4 g of chlorobenzene. The mixed solution obtained was heated to 45-55° C. while being stirred, and 153.5 g (1 mol) of phosphorus oxychloride was added dropwise into the mixed solution over 1 hour. After the addition of phosphorus oxychloride was completed, the mixed solution was heated up to 75° C. over 1 hour, and a reaction was allowed to proceed at the same temperature (75° C.) over 1 hour to recover 65.7 g of hydrochloric acid generated. Thereafter, the pressure was reduced to 26.6 kPa at the same temperature (75° C.) and was maintained for 2 hours, and the remaining hydrochloric acid was recovered as gas. Thus, 298.9 g of a reaction mixture was obtained.

The reaction mixture obtained was cooled down to a room temperature, and 161.5 g (0.95 mol) of 2-hydroxybiphenyl, 0.9 g of anhydrous magnesium chloride and 145.6 g of chlorobenzene were added to it. This mixed solution was heated to 65° C. to 75° C. while being stirred. 106.1 g (1.05 mol) of triethylamine was then added dropwise to the mixed solution over 1 hour. Thereafter, a reaction was allowed to proceed at the same temperature (75° C.) over 1 hour to obtain a mixed solution of 5,5-dimethyl-2-(2'-phenylphenoxy)-1,3,2-dioxaphosphorinane-2-oxide (LC purity: 96.0%).

(Post Treatment)

Aqueous hydrochloric acid solution corresponding to an excess triethylamine was added to the mixed solution obtained, to perform neutralization treatment at 85° C. The flask was left standing and then an oil phase was extracted. Next, the oil phase obtained was washed with 85° C. water, and dehydration was performed. The oil phase obtained was gradually cooled down to obtain 259.8 g (LC purity: 98.8%) of white needle crystal. Assuming all the crystal was the objective compound, the yield was 86.0%.

Comparative Example 2

A reaction was attempted similarly to Comparative Example 1, except for the fact that triethylamine was not used.

However, when the solution after the reaction was completed was measured by GPC and the amount of hydrochloric acid recovered was confirmed, only the peak of the raw material was observed and the reaction did not proceed at all.

Comparative Example 3

Step 1

2-biphenylylphosphorodichloridate was obtained in a similar manner as in the step 1 in Example 1.

Step 2

Next, the 2-biphenylylphosphorodichloridate obtained in the step 1 was cooled down to 60° C., and 195.8 g (2.08 mol) of phenol was added thereto. This mixed solution was heated up to 130° C. over 5 hours under a nitrogen atmosphere while being stirred, and the reaction was allowed to proceed over 8 hours under a reduced pressure (20 kPa) at the same temperature (130° C.).

This reaction solution was cooled down to 80° C. Nitrogen was then introduced to set the pressure inside the flasks normal. At the same temperature (80° C.), washing was performed successively with 1.6% hydrochloric acid and 0.7% aqueous sodium carbonate solution, and washing with water was performed in the end. Furthermore, steam distillation was performed at 140° C. under a reduced pressure (2.7 kPa) to remove low boiling point components from the reaction product. Thus, 382.8 g (LC purity: 92.9%) of a colorless, transparent liquid comprising 2-biphenylyldiphenylphosphate as a main component was obtained. Assuming all the liquid was the objective compound, the yield was 95.1%.

Comparative Example 4

Step 1

2-biphenylylphosphorodichloridate was obtained in a similar manner as in the step 1 in Example 1.

Step 2

Next, a four-necked 2-liter flask, equipped with a stirrer, a thermometer, a dropping funnel, and a reflux condenser, was filled with 140.8 g (1.9 mol) of n-butanol and 592.1 g of toluene. This mixed solution was heated up to 90° C. over 1 hour while being stirred under a nitrogen atmosphere, and then 290.8 g of the 2-biphenylylphosphorodichloridate obtained in the step 1 was added at 90° C. over 2 hours. Thereafter, the mixed solution was heated to 105° C. over 1 hour, and it was stirred for 1 hour at the same temperature (105° C.) to attempt a reaction.

As a result of an analysis of the solution after the completion of the reaction by LC, however, only about 50% of the objective product, or 2-biphenylyldibutylphosphate, was obtained, and the rest of the product obtained were butyl chloride and biphenylylbutylphosphate decomposed by hydrochloric acid.

Comparative Example 5

Step 1

2-biphenylylphosphorodichloridate was obtained in a similar manner as in the step 1 in Example 1.

Step 2

Next, a four-necked 2-liter flask, equipped with a stirrer, a thermometer, a dropping funnel, and a reflux condenser, was filled with 85.6 g (0.95 mol) of 1,4-butanediol and 592.1 g of toluene. This mixed liquid was heated up to 90° C. over 1 hour under a nitrogen atmosphere while being stirred, and then 290.8 g of the 2-biphenylylphosphorodichloridate obtained in the step 1 was added at 90° C. over 2 hours. Thereafter, the mixed liquid was heated to 105° C. over 1 hour, and it was stirred for 1 hour at the same temperature (105° C.) to attempt a reaction.

As a result of an analysis of the solution after the completion of the reaction by LC, however, the objective product, or 2-(2'-phenylphenoxy)-1,3,2-dioxaphosphepane-2-oxide, was scarcely obtained, but a high-molecular weight component crosslinked with 1,4-butanediol was obtained.

TABLE 1

| | | | LC analysis | | |
| | purity | yield | monomer | dimer | trimer | side reaction product |
| --- | --- | --- | --- | --- | --- | --- |
| Example 1 | 98.5 | 95.2 | 98.5 | 1.1 | 0.4 | |
| Example 2 | 98.1 | 93.5 | 98.1 | 1.5 | 0.4 | |
| Example 3 | 98.9 | 95.3 | 98.9 | 0.8 | 0.3 | |
| comparative example 1 | 98.8 | 86.0 | 98.8 | 1.0 | 0.2 | |
| comparative example 2 | no reaction | no reaction | | | | |
| comparative example 3 | 92.9 | 95.1 | 92.9 | 6.6 | 0.5 | |
| comparative example 4 | 51.8 | not able to isolate | 51.8 | | | 48.2 |
| comparative example 5 | 28.1 | not able to isolate | 28.1 | | | 71.9 |

[Chemical Formula 17]

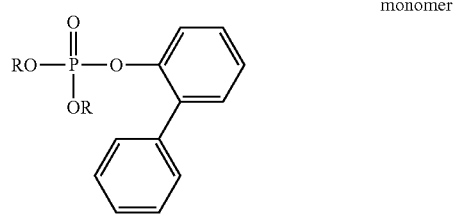

monomer

-continued

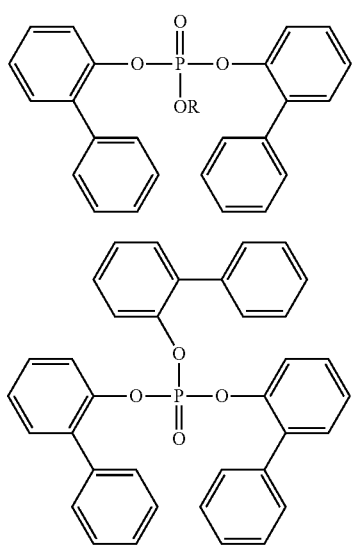

dimer trimer

The R group is a corresponding alkyl group or aryl group described in the Examples and Comparative Examples.

In Examples 1 to 3 as well as Comparative Examples and 2, 5,5-dimethyl-2-(2'-phenylphenoxy)-1,3,2-dioxaphosphorinane-2-oxide was produced.

From the results in the Table, the monomer, which is the objective product, was obtained as a main compound with a favorable yield and purity in Examples 1 to 3. From this result, it is considered that the reaction with a propanediol compound in the step (2) made it possible to form the stable 6-membered ring structure and the product having high purity was obtained.

On the other hand, in Comparative Example 1 where amine was used, re-crystallization was necessary to obtain the product having high purity, and the yield in that case was such a low value of 86%. In addition, in Comparative Example 2, the reaction was attempted without amine, but the reaction did not proceed at all.

Specifically, it can be said that when the compound of the Formula (V) is produced as an objective compound, the production method according to the present invention is significantly excellent and optimal.

In Comparative Example 3, phenol was used instead of 2,2-dimethyl-1,3-propanediol. As a result, while the reaction proceeded, the purity resulted in being lower compared to the purity in Examples 1 to 3.

In Comparative Example 4, n-butanol was used, and the product was decomposed due to the hydrochloric acid produced as a by-product, resulting in low yield and purity.

Furthermore, in Comparative Example 5, when 1,4-butandiol was used to allow the reaction to proceed, a cyclization reaction and a crosslinking reaction simultaneously proceeded, resulting in quite low purity.

In other words, it is shown that in Comparative Examples 3 to 5, when the reaction was allowed to proceed with phenol, n-butanol and 1,4-butandiol respectively, instead of 2,2-dimethyl-1,3-propanediol, in Examples 1 to 3 and Comparative Examples 1 and 2, the purity dropped and side reactions occurred to prevent the proceeding of the main reaction, resulting in the decrease in the yield.

Thus, from the foregoing, the production method according to the present invention is a production method that specifically exerts effects and is most suitable, only in a case where the compound of the Formula (V) is produced as an objective compound.

INDUSTRIAL APPLICABILITY

According to the present invention as described above, a phosphorus compound having both an aromatic substituent and a phosphorinane backbone can be produced without using an expensive hydrogen halide scavenger, such as triethylamine, tributylamine or pyridine, without going through a complicated post treatment step or a step of recovering a solvent, and with lower cost and with a more favorable yield and purity compared to conventional methods. Thus, the present invention is extremely useful in the technical field relating to the production of flame retardants.

The invention claimed is:

1. A method for producing a phosphoric acid ester, comprising:

a step (1):

a step of allowing phosphorus oxytrihalide represented by Formula (I)

[Chemical Formula 18]

(I)

(wherein X is halogen)

to react with a phenol compound or naphthol compound represented by Formula (II)

[Chemical Formula 19]

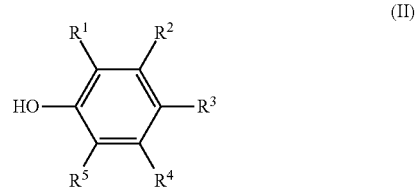

(II)

(wherein $R^1$, $R^2$, $R^3$, $R^4$ and $R^5$ are independent from one another, and are a hydrogen atom, a straight or branched-chain $C_{1-6}$ alkyl group, or a $C_{6-12}$ aryl group which may be substituted with a straight or branched-chain $C_{1-4}$ alkyl group, and alternatively $R^1$ and $R^2$, $R^2$ and $R^3$, $R^3$ and $R^4$, or $R^4$ and $R^5$ may form a 6-membered ring together with the carbon atoms of the benzene ring to which these groups are bound, provided that $R^1$, $R^2$, $R^3$, $R^4$ and $R^5$ are not hydrogen atoms at the same time), at a molar ratio of 1.1-3.0:1 in the presence of a metal halide, to produce a mono-substituted phosphorodihalidate represented by Formula (III)

[Chemical Formula 20A]

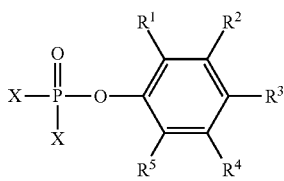

(wherein X, $R^1$, $R^2$, $R^3$, $R^4$ and $R^5$ have the same meaning as the above-described meaning); and a step (2):
a step of allowing the mono-substituted phosphorodihalidate obtained in the step (1) represented by the Formula (III)

[Chemical Formula 20B]

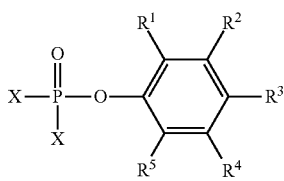

to react with a diol compound represented by Formula (IV)

[Chemical Formula 21]

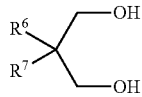

(wherein $R^6$ and $R^7$ are independent from each other, and are a hydrogen atom, a straight or branched-chain $C_{1-6}$ alkyl group, or a $C_{6-12}$ aryl group which may be substituted with a straight or branched-chain $C_{1-4}$ alkyl group) so as to perform a dehydrohalogenation reaction to produce a phosphorus compound represented by Formula (V)

[Chemical Formula 22]

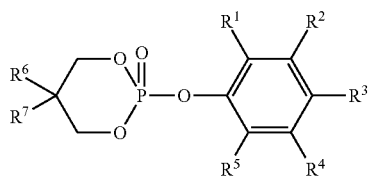

(wherein $R^1$, $R^2$, $R^3$, $R^4$, $R^5$, $R^6$ and $R^7$ have the same meaning as the above-described meaning).

2. The method for producing a phosphoric acid ester according to claim 1, wherein the ratio of the amount of the diol, represented by the Formula (IV), used in the step (2) is 0.90 to 0.99 molar equivalent based on 1 mole of a halogen atom of the mono-substituted phosphorodihalidate represented by the Formula (III).

3. The method for producing a phosphoric acid ester according to claim 1, wherein the metal halide in the step (1) is magnesium chloride and/or aluminum chloride.

4. The method for producing a phosphoric acid ester according to claim 1, wherein the reaction in the step (1) is performed at a reaction temperature of 80° C. to 140° C.

5. The method for producing a phosphoric acid ester according to claim 1, wherein the step (1) comprises a step of removing unreacted phosphorus oxytrihalide after a reaction between the phosphorus oxytrihalide and the phenol compound or naphthol compound.

6. The method for producing a phosphoric acid ester according to claim 5, wherein the removal of the unreacted phosphorus oxytrihalide in the step (1) is performed at a temperature of 80° C. to 140° C. and under a reduced pressure of 20 kPa or less.

7. The method for producing a phosphoric acid ester according to claim 1, wherein the reaction in the step (2) is performed at a reaction temperature of 70° C. to 160° C.

8. The method for producing a phosphoric acid ester according to claim 1, wherein in the step (2), a solvent is used in an amount of 0.5 to 6 fold by weight to that of the diol represented by the Formula (IV), and the solvent is one or more solvents selected from the group consisting of toluene, xylene, chlorobenzene, and o-dichlorobenzene.

9. The method for producing a phosphoric acid ester according to claim 1, further comprising a step of purifying the phosphoric acid ester represented by the Formula (V) obtained in the step (2), wherein at least one type of treatment is selected from the group consisting of acid washing, alkaline washing, water washing, reduced pressure distillation, and recrystallization.

10. The method for producing a phosphoric acid ester according to claim 1, further comprising a step of removing impurities in the phosphoric acid ester represented by the Formula (V) obtained in the step (2), at a temperature of 70° C. to 160° C. and under a reduced pressure of 20 kPa or lower.

11. The method for producing a phosphoric acid ester according to claim 1, wherein the phosphorus oxytrihalide represented by the Formula (I) in the step (1) is phosphorus oxychloride or phosphorus oxybromide.

12. The method for producing a phosphoric acid ester according to claim 1, wherein the phenol compound or naphthol compound represented by the Formula (II) in the step (1) is 2-hydroxybiphenyl.

13. The method for producing a phosphoric acid ester according to claim 1, wherein the diol compound represented by the Formula (IV) in the step (2) is 2,2-dimethyl-1,3-propanediol.

* * * * *